United States Patent
Burkinshaw

(10) Patent No.: US 6,214,052 B1
(45) Date of Patent: Apr. 10, 2001

(54) TIBIAL COMPONENT WITH A REVERSIBLE, ADJUSTABLE STEM

(75) Inventor: Brian Burkinshaw, Pflugerville, TX (US)

(73) Assignee: Sulzer Orthopedics Inc., Austin, TX (US)

( * ) Notice: Subject to any disclaimer, the term of this patent is extended or adjusted under 35 U.S.C. 154(b) by 0 days.

(21) Appl. No.: 09/233,652

(22) Filed: Jan. 19, 1999

(51) Int. Cl.[7] .................................................. A61F 2/38
(52) U.S. Cl. ..................................... 623/20.34; 623/20.15
(58) Field of Search ........................... 623/20.15, 20.34, 623/20.32, 18.11, 22.41, 22.42

(56) References Cited

U.S. PATENT DOCUMENTS

| 4,219,893 | 9/1980 | Noiles | 3/1.911 |
|---|---|---|---|
| 4,301,553 | 11/1981 | Noiles | 3/1.911 |
| 4,624,673 | 11/1986 | Meyer | 626/16 |
| 4,634,444 | 1/1987 | Noiles | 623/20 |
| 4,822,366 | * 4/1989 | Bolesky | 623/20.34 |
| 4,846,839 | 7/1989 | Noiles | 623/18 |
| 4,888,021 | 12/1989 | Forte et al. | 623/20 |
| 4,938,769 | 7/1990 | Shaw | 623/20 |
| 4,944,757 | * 7/1990 | Martinez et al. | 623/20.34 |
| 5,011,496 | 4/1991 | Forte et al. | 623/20 |
| 5,152,796 | * 10/1992 | Slamm | 623/20.34 |
| 5,271,737 | 12/1993 | Baldwin et al. | 623/20 |
| 5,290,313 | 3/1994 | Heldreth | 623/20 |
| 5,782,920 | * 7/1998 | Colleran | 623/18 |
| 5,879,391 | * 3/1999 | Slamin | 623/20.34 |

* cited by examiner

Primary Examiner—Bruce Snow
(74) Attorney, Agent, or Firm—Philip S. Lyren

(57) ABSTRACT

A tibial prosthetic implant with a reversible offset stem includes a base and a boss extending from the base. A reversible keel member includes a first end attached to the boss and a second end including an offset stem receiver. A stem includes a stem attachment extending at an angle from a first end thereof and connected to the offset stem receiver such that attaching the angled end of the stem to the offset stem receiver when the keel is in a first position, offsets the stem in a first direction, whereas, attaching the angled end of the stem to the offset stem receiver when the keel is in a second position, reversed from the first position, offsets the stem in a second direction.

13 Claims, 5 Drawing Sheets

TIBIAL COMPONENT WITH A REVERSIBLE, ADJUSTABLE STEM

BACKGROUND

The disclosures herein relate generally to orthopedic implants and more particularly to a tibial prosthetic implant having an adjustable stem.

A frequently acknowledged limitation related to stemmed tibia components is that they do not adequately address the medial anatomic location of the intramedullary canal. Presently known devices provide only a fixed amount of either anterior and/or medial offset. Problems presented to orthopedic surgeons regarding tibial prosthetic implants include centering a baseplate to preferably cover 85% of the proximal tibia. This is difficult because the tibia is not symmetrical and the intramedullary canal does not extend down the center of the tibia. Therefore, the stem component must be offset relative to the baseplate. This combination presents difficulties which have been dealt with in various ways.

U.S. Pat. Nos. 4,219,893 and 4,301,553 each disclose a prosthetic knee joint of the hinged type which permits rotation of the bones in two planes and has means for attaching the device to the bones as well as coupling means. The attaching means for the tibia is in the form of a flanged sleeve in which a flanged stem element is adapted to be rotatably received. The stem element and the attaching means for the femur are coupled together so that they are permitted to undergo relative rotation in the plane of flexion. The rotation of the stem in the sleeve about the axis of the shaft of the tibia permits rotational movement of the pair of bones in the axial plane. The stem is free to distract from the sleeve while maintaining alignment to insure proper reengagement. Bearing surfaces on the stem and sleeve elements are adapted to engage so that the large forces exerted on the implanted device by reason of the knee's function and mechanics are distributed over the substantial area of the congruent thrust bearing surfaces. Non-hinged knee joints with congruent bearing surfaces allow flexion and tibial rotation.

U.S. Pat. No. 4,624,673 discloses a two part system for fastening a dental prosthesis to the jaw bone having as a first part, an externally threaded thin wall sleeve which resides entirely within the jaw bone. The threads or other surface features are confined to the area near the point where the prosthesis enters the jaw bone. The sleeve has integrally, or accommodates, a non-threaded stem which extends relatively deeply into the jaw bone. The inner bore of the sleeve is a cone of a mechanically self locking taper. The second part, which extends outwardly from the jaw bone through the gum tissue, has a mating external taper which is driven within the sleeve to be locked therein. The second part supports an artificial tooth, bridge or other dental appliance. The concept also is applicable to a prosthetic device for any body joint.

In U.S. Pat. No. 4,634,444, an artificial joint having stepped convex and concave bearing surfaces is provided. The stepped configuration prevents the bearing surfaces from sliding past one another along their axis of rotating and thus stabilizes the joint against lateral dislocations. The stepped bearing surfaces faces may be employed in an artificial knee joint, and the joint is further stabilized against dislocations corresponding to the femur moving anteriorly with respect to the tibia.

In U.S. Pat. No. 4,846,839, a joint prosthesis component for implantation in the end of a bone is provided. The component comprises a collar which holds a stem in a fixed position. The envelope of the bone engaging surface of the collar has a shape and size which corresponds to the shape and size of the cancellous bone at the end of the bone in that the envelope of the collar is more ovoid than round, having a large diameter which lies medially to laterally and a smaller diameter which lies anteriorly to posteriorly when the component is implanted in the end of the bone. The collar, but not the stem, may be porous coated.

In U.S. Pat. Nos. 4,888,021 and 5,011,496, a prosthetic knee joint is provided having an extended position, an intermediate position, and a flexed position. The motion of the joining includes a minor segment from the extended positions to the intermediate position, and a major segment from the intermediate position to the flexed position. The center of pressure between the femoral component and the tibial component moves rearward on the tibia during the minor segment. During the major segment, the joint flexes about an axis of rotation with the bearing surfaces on the femoral and tibial components being in congruent engagement. The distal surface of the femoral component includes two rails for engagement with a patellar prosthesis. The contour of the rails is either a straight line or a concave curve to provide line contact between the rails and the patellar prosthesis. The patellar prosthesis may include a saddle-shaped surface so that the prosthesis and each of the rails can make contact over an area extending along the length of the rail.

In U.S. Pat. No. 5,271,737, a tibial prosthetic implant includes a base or base plate with an offset tibial stem. The base includes an inferior surface adapted to abut a resected surface of a patient's tibia and forms a base for articulating surfaces adapted to articulate with the patient's femoral condyles. The longitudinal center axis of the tibial stem extends from the inferior surface of the base and is offset from the center of the base. The offset places the stem in position to extend into the central canal of the tibia so that it does not substantially interfere with the cortical bone when the inferior surface of the base substantially abuts and aligns with the resected surface of the tibia.

Therefore, what is needed is a modular tibial component having the ability to medially and anteriorly offset the stem relative to the geometric centerline of the proximal tibial plateau, in varying amounts, based on a patient's anatomy and preferably be usable on either the right or left tibia to reduce the number of parts variations required to provide a suitable tibial prosthetic implant.

SUMMARY

One embodiment, accordingly, provides a reversible modular tibial component so that it can be applied either as a right or left component, and also allow for posterior tilt to further address normal anatomic considerations. To this end a modular tibial component includes a base and a keel member reversibly attachable to the base and having an offset stem receiver. A stem includes a stem attachment extending from a first end thereof for attachment to the offset stem receiver.

A principal advantage of this embodiment is that a surgeon is provided with the intra-operative advantage of choosing the amount of relative medial and anterior offset necessary for a given patient.

BRIEF DESCRIPTION OF THE DRAWING FIGURES

DETAILED DESCRIPTION

Figure 1:
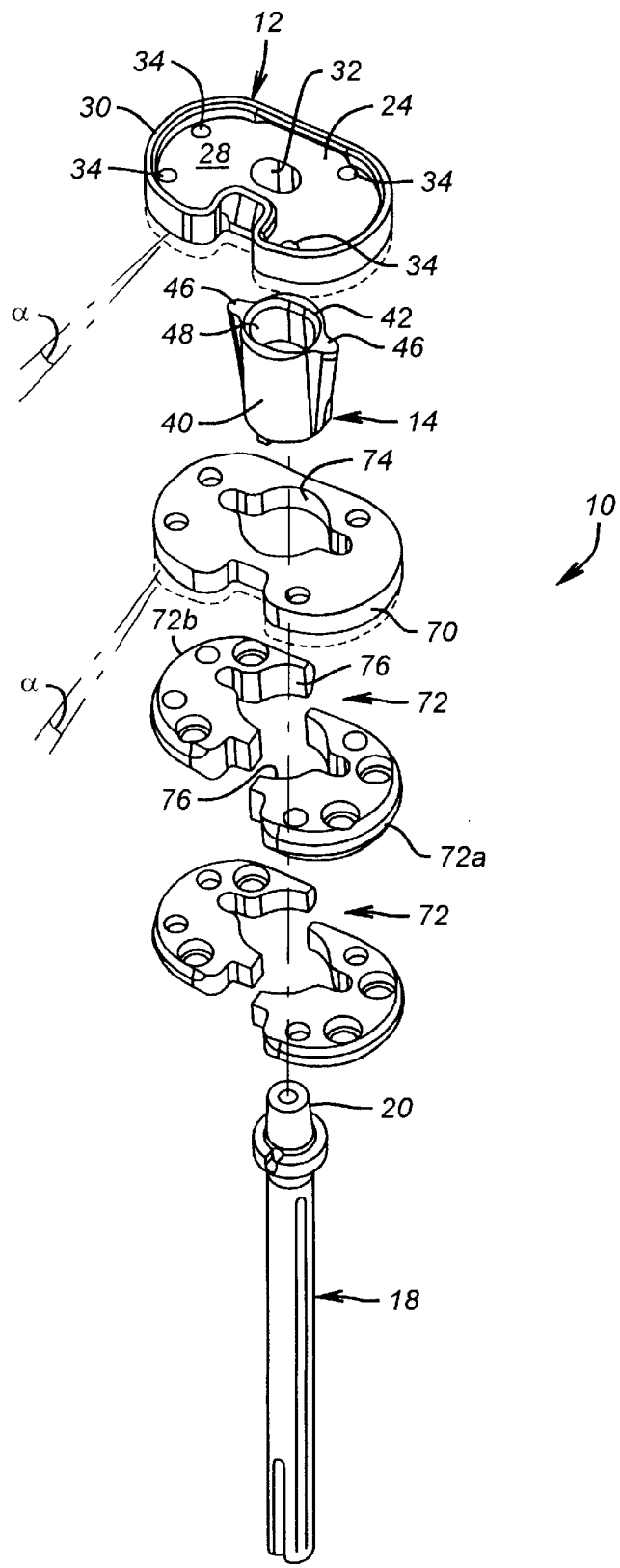
FIG. 1 is an exploded isometric view illustrating an embodiment of a modular tibial component.

A modular tibial component, FIG. 1 is generally designated 10 and includes a base member 12 and a keel member 14 which is reversibly attachable to the base member 12. The keel member includes an offset stem receiver 16. A stem 18 includes an attachment 20 extending from a first end 22 thereof, for attachment to the offset stem receiver.

Figure 2:
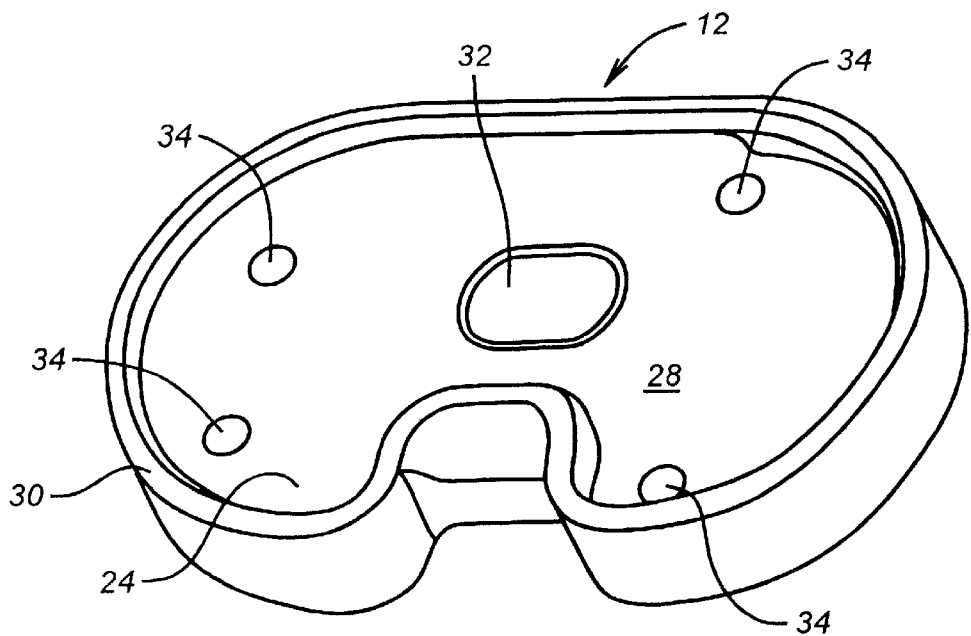
FIG. 2 is an isometric view illustrating an embodiment of one side of a base member.
Figure 3:
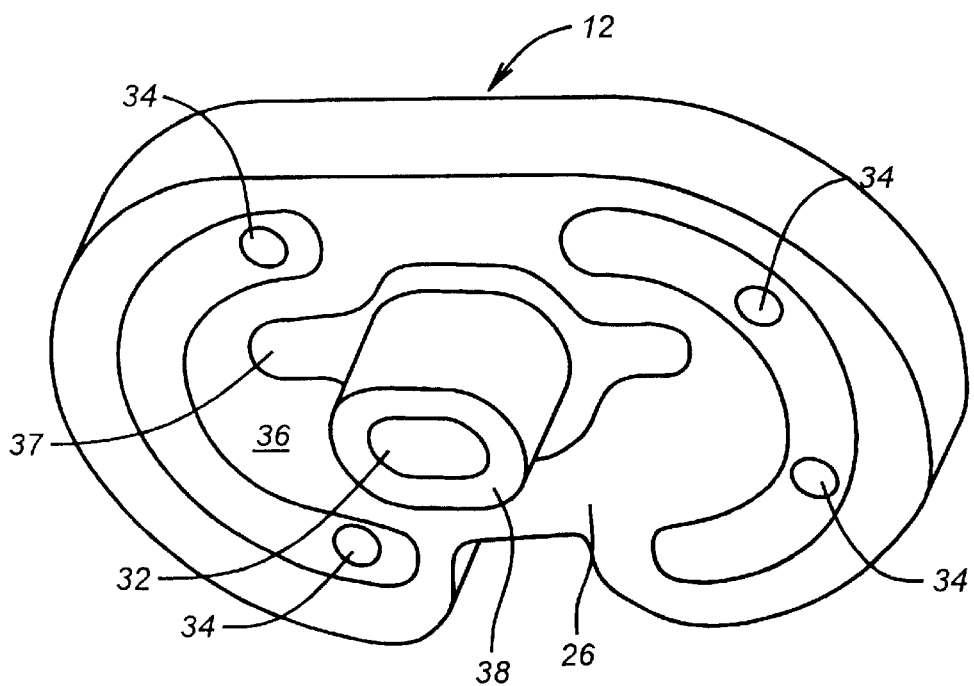
FIG. 3 is an isometric view illustrating an embodiment of an opposite side of the base member.

Base member 12 is generally oblong and includes a first side 24, FIGS. 1 and 2, and a second side 26, FIG. 3. First side 24, FIGS. 1 and 2 includes a generally planar surface 28 and a peripheral raised rim 30. An oblong, substantially central aperture 32 is provided for receiving a threaded fastener for attachment to the stem 18, to be discussed below. A plurality of spaced apart apertures 34 are provided to receive threaded fasteners for attaching one or more spacers to second side 26, FIG. 3, to be discussed below. Second side 26 includes a generally planar surface 36 which may include a shaped recess 37. A connector boss 38 extends from surface 36 and is generally oblong. Aperture 32 extends through boss 38. Apertures 34 extend through base member 12 to surface 36. Second side 26 may include an inferior surface taper angle about 0° to about 12 °.

Figure 4:
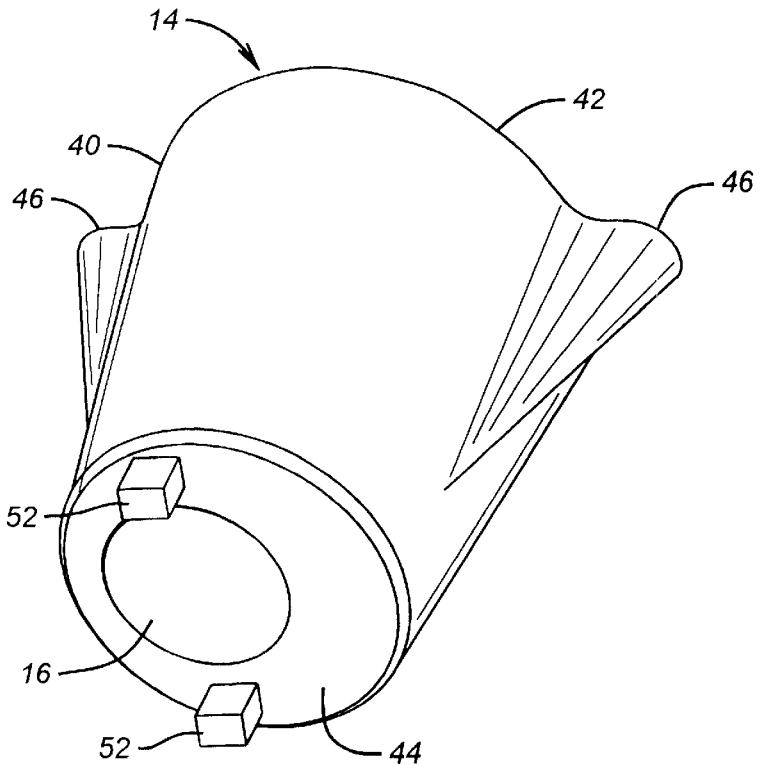
FIG. 4 is an isometric view illustrating an embodiment of a keel member.
Figure 5:
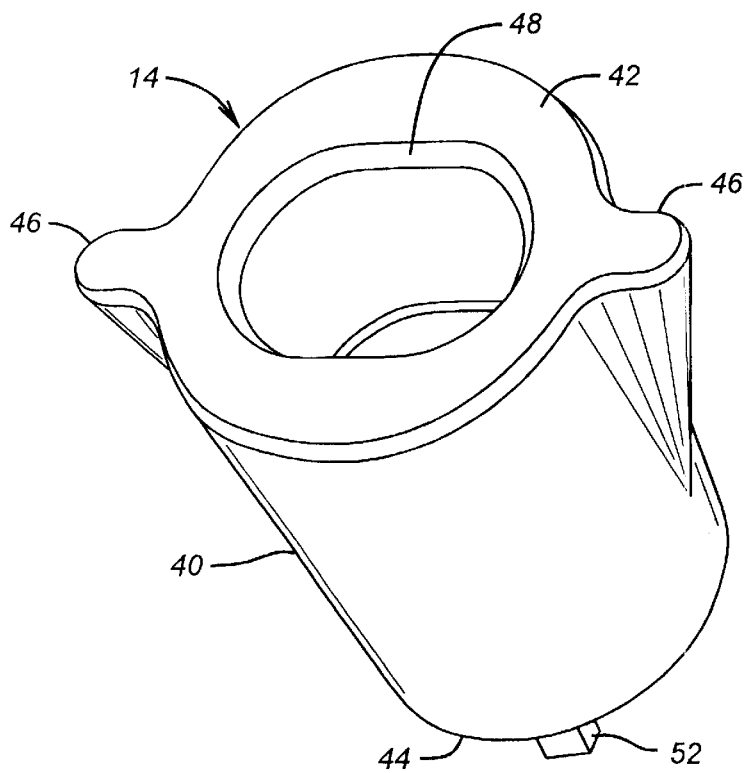
FIG. 5 is another isometric view illustrating an embodiment of the keel member.
Figure 4A:
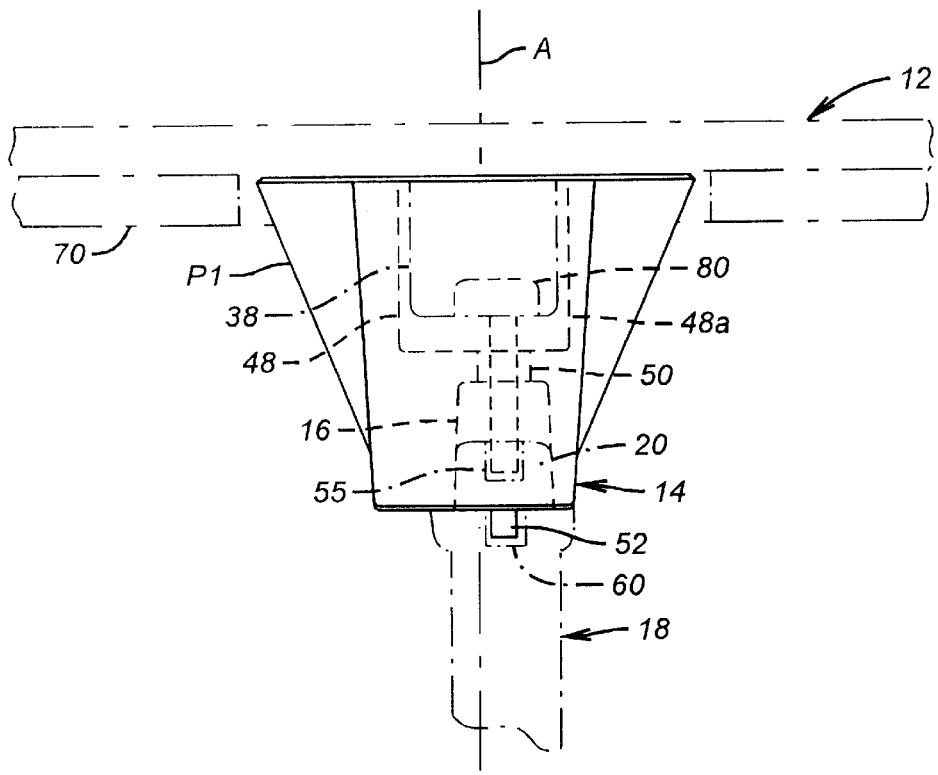
FIG. 4a is a partial graphical side view illustrating an embodiment of an assembled base, spacer, keel and stem, connected in a first orientation.
Figure 4B:
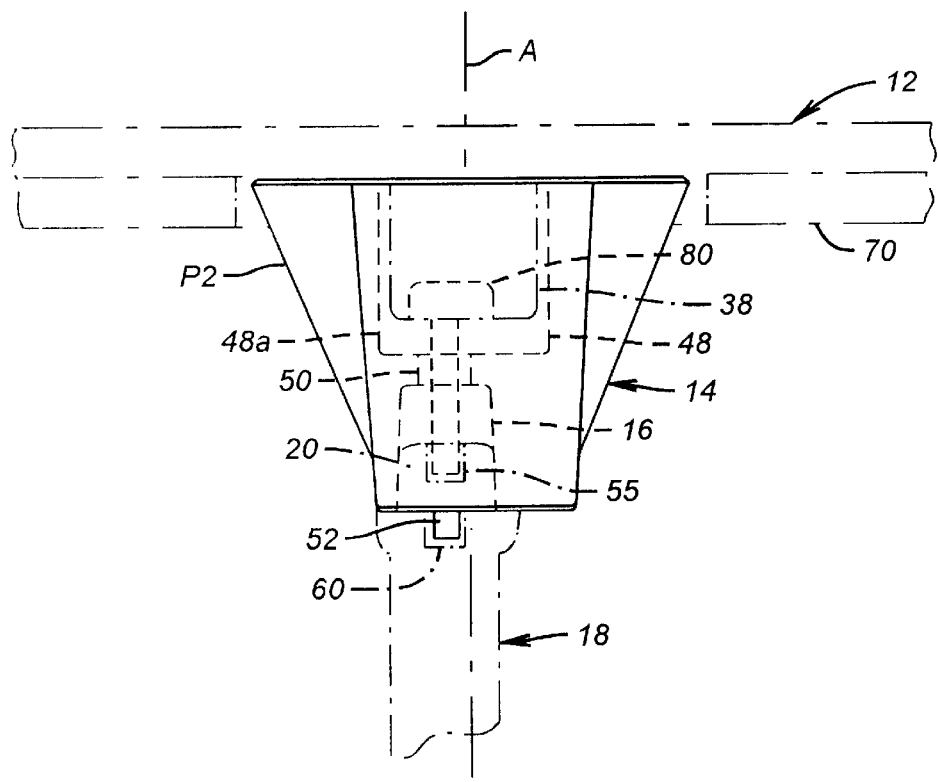
FIG. 4b is a partial graphical side view illustrating the assembled base, spacer, keel and stem, connected in a second orientation.

Keel member 14, FIGS. 4 and 5, includes a generally cylindrical main body portion 40 which extends from a first end 42 to a second end 44. First end 42 includes a pair of opposed fins 46 extending radially therefrom. A recess 48 in first end 42 is generally oblong and sized to receive boss 38. The oblong shape of the boss 38 and the recess 48 provide for a non-rotating mating engagement when keel member 14 is engaged with base member 12 and boss 38 is received in recess 48. Also, first end 42 including fins 46, seats in recess 37 when keel member 14 is engaged with base member 12. Second end 44 of keel member 14 includes an offset stem receiver 16 which is a generally cylindrical recess formed in second end 44, and interconnects with recess 48 by means of a fastener aperture 50, FIGS. 4a and 4b. Alignment of stem receiver 16 and fastener aperture 50 is offset to one side 48a of recess 48. In this manner, keel member 14 is reversibly connectable to boss 38 of base member 12 so that stem receiver 16 may be offset relative to base member 12. Keel member 14 is depicted in a first position P1 in FIG. 4a, and is depicted in a second position P2 in FIG. 4b, in which keel member 14 is reversed or oriented 180° to the position P1 depicted in FIG. 4a. As a result of orienting keel member 14 in positions P1 and P2, stem receiver 16 is positionable on opposite sides of a centroidal axis A of keel member 14.

A pair of tabs 52, FIG. 4, are diametrically opposed on opposite sides of stem receiver 16 and extend from second end 44 of keel member 14.

Figures 6, 7:
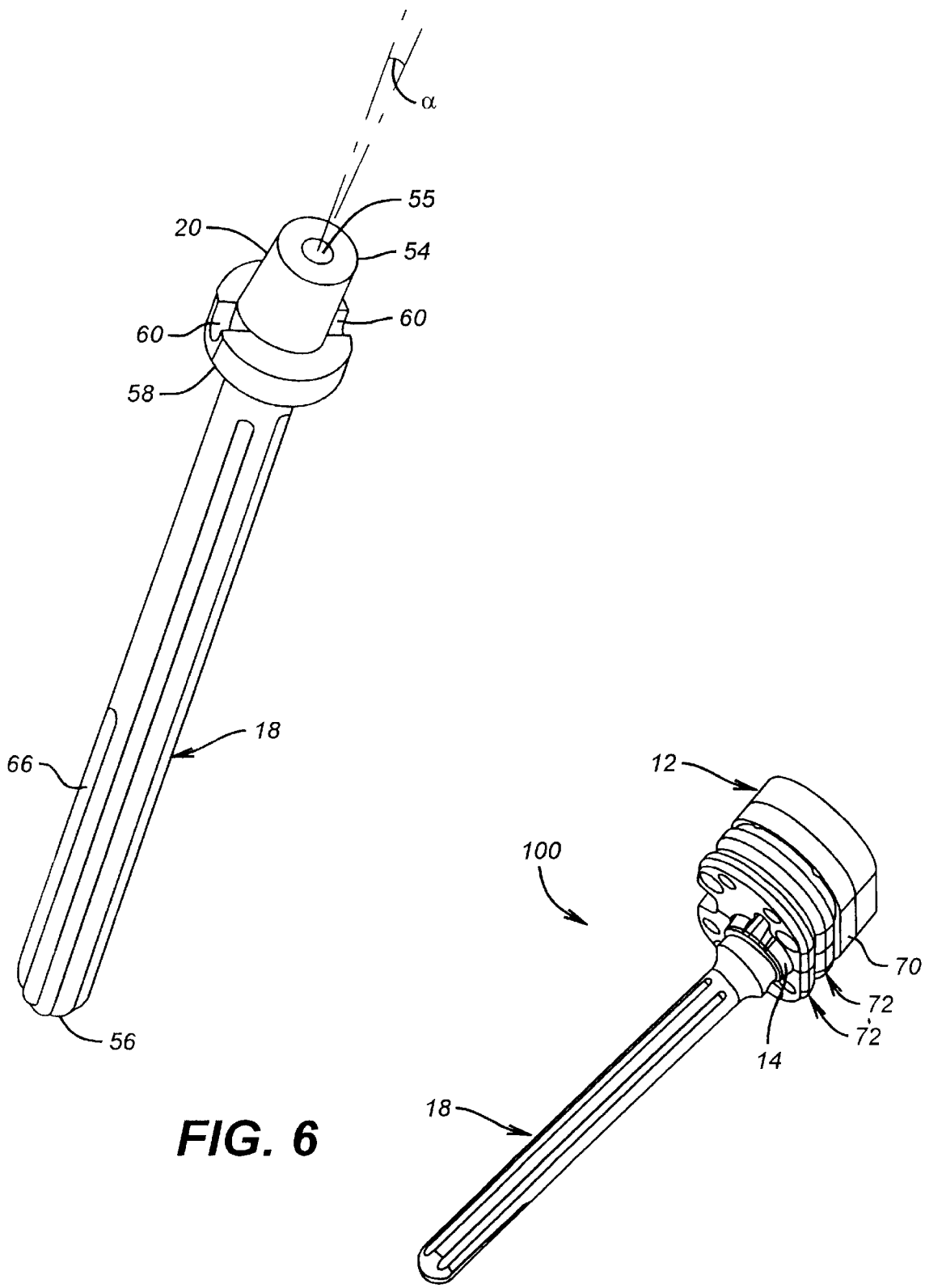
FIG. 6 is an isometric view illustrating an embodiment of a stem member.
FIG. 7 is an isometric view illustrating an embodiment of the assembled modular tibial component.

Stem 18, FIG. 6, includes a first end 54 and a tapered second end 56. First end 54 includes the attachment 20 extending therefrom at an angle of from about 0° to about 12°, and preferably to about 7° adjacent a circumferential flange 58. The angle provides for variation in the natural anatomical posterior slope of the tibia, and also allows for a selective range of posterior slope desired by the surgeon. Flange 58 includes a pair of diametrically opposed notches 60 formed therein for receiving tabs 52 of keel member 14, thus assuring proper orientation of stem 18. It is to be understood that tabs 52 could be formed to extend from flange 58 and notches 60 could be formed in second end 44 of keel member 14 to achieve the same orientation result for stem 18. Stem 18 also includes a plurality of longitudinal flutes 62 formed in a surface 64 thereof to provide for an anti-rotation means within the intramedullary canal by creating a macro-lock within the internal diameter (I.D.) of the bone and/or the bone cement. Second end 56 of stem 18 includes an elongated slot 66 formed therein to allow for reduction in the I.D. of the bone, and to create a reverse clothespin or wedge effect. Slot 66 also reduces stiffness at end 56 of stem 18. First end 54 of stem 18 includes a threaded aperture 55 for receiving a threaded fastener therein to secure the base 12, keel 14 and stem 18 together.

A spacer or a plurality of spacers may be attached to base 12 and used to accommodate a distal femoral surface which has been prepared in consideration of significant bone loss. For example, a one piece spacer 70, FIG. 1, or a two piece spacer 72 including a first portion 72a and a second portion 72b may be used. If desired, a side 71 of spacer 70 may include an inferior surface taper angle of from about 0° to about 12°. Although not shown, the taper angle can also be applied to spacer 72. An opening 74 in spacer 70 is provided and shaped accordingly to accommodate keel member 14. In the case of the two piece spacer, each portion 72a and 72b, includes a composite opening 76 78 respectively, which combine to accommodate keel member 14 in a similar manner to opening 74 of spacer 70. As a result, an assembled tibial component 100, FIG. 7, may include base 12, keel 14, stem 18, and in an exaggerated form, a plurality of spacers including one piece spacer 70 and a pair of two piece spacers 72. Referring again to FIGS. 4a and 4b, it can be seen that base 12, spacer 70, keel 14 and stem 18 are retained together by a fastener 80. Boss 38 extends through spacer 70 and into recess 48. Attachment 20 extends into receiver 16. Fastener 80 engages boss 38 and extends through fastener aperture 50 to threadably engage threaded aperture 55 of attachment 20. Tabs 52 extend into engagement with notches 60.

In operation, a metal tibial baseplate component, either symmetric or asymmetric, includes a locating feature on the inferior surface that is positioned on or about the medial/lateral centerline and in the anterior ⅓ of the baseplate, along the anterior/posterior centerline. The locating feature includes a through-hole to accommodate a screw used to assemble various mating stem components. The locating feature would ideally be an external, straight walled boss-type feature. This same locating feature may have a male tapered exterior, or female tapered interior, to accommodate an intermediate assembly having a corresponding, mating Morse-like taper. The intermediate assembly, or the stem base, is of sufficient diameter and length to allow for a mating feature on the superior end surface, corresponding to the baseplate locating feature, and another internal or external tapered feature on its inferior end to accept various stem components. Additionally, the tapered feature on the inferior surface can be placed at various distances, medially offset from its medial/lateral centerline, in order to accurately position the placement of a stem attachment in the anatomically correct location for placement in the tibial intramedullary canal. The inferior tapered feature can also be anteriorly, or posteriorly, offset from its anterior/posterior centerline, with optional medial offset to allow further adjustment for location of the stem to match the patient's anatomy.

Preferably, a tapered stem attachment that mates with the corresponding taper, is provided on the inferior surface of the stem base. The stem attachment includes a taper that is produced at an acute angle from the axial centerline of the stem, ranging from 0 to 12 degrees. Both the stem base and stem include a keying feature to provide for the correct anatomic rotation of the stem relative to the baseplate and desired anatomic posterior slope. This method of providing posterior slope allows the stem base and stems to be reversible, thus allowing for their use in either a left or right application. An alternative for the introduction of posterior slope includes the application of varying degrees of slope, ranging from 0 to 12 degrees, being placed on the superior surface of the stem base, thus allowing the use of similar stems having tapers that are concentric to their central axis. Also, a protruding boss feature or entire inferior surface of the baseplate, may be produced at an acute angle relative to the superior surface of the baseplate, ranging from 0 to 12 degrees, thus allowing the use of similar stem bases and stems having attachment features and or tapers that are concentric to their central axis. The desired result may be achieved by providing, either singly or in combination, a base having a tapered surface, a spacer member having a tapered surface, and the stem attachment extending from the stem at an angle.

As a result, one embodiment provides a modular tibial component including a base and a keel member reversibly attachable to the base and having an offset stem receiver. A stem includes a stem attachment extending from a first end thereof for attachment to the offset stem receiver.

Another embodiment provides a reversible tibial component including a base and a keel member attached to the base in one of a first or second position. The keel member has an offset stem receiver. A stem includes a stem attachment extending at an angle to the offset stem receiver.

Another embodiment provides a tibial prosthetic implant with a reversible offset stem including a base having a boss extending therefrom. A reversible keel member has a first end attached to the boss and a second end including an offset stem receiver. A stem includes a stem attachment extending at an angle from a first end thereof and connected to the offset stem receiver.

A further embodiment provides a method of mounting a tibial prosthetic implant with a reversible offset stem. A boss is formed on a base member of the implant. A first end of a keel member is attached to the boss in a first or a second position. An offset stem receiver is formed on a second end of the keel member. An angled end of a stem is attached to the offset stem receiver when the keel member is in the first position for offsetting the stem in a first direction. Alternatively, the angled end of the stem is attached to the offset stem receiver when the keel member is in the second position for offsetting the stem in a second direction, opposite the first direction.

As it can be seen, the principal advantages of these embodiments are that the surgeon is provided with the intra-operative advantage of choosing the amount of relative medial and anterior offset for a given patent, within a range of available options, along with the ability to accommodate posterior slope to match that of the patient. As a result, a modular tibial component is provided having the ability to medially and anteriorly offset the stem relative to the geometric centerline of the proximal tibial plateau, based on a patient's anatomy. In addition, the component is reversible so that it can be applied either as a right or left component, and allow for posterior tilt.

Although illustrative embodiments have been shown and described, a wide range of modification, change and substitution is contemplated in the foregoing disclosure and in some instances, some features of the embodiments may be employed without a corresponding use of other features. Accordingly, it is appropriate that the appended claims be construed broadly and in a manner consistent with the scope of the embodiments disclosed herein.

What is claimed is:

1. A modular tibial component comprising:
    a base;
    a keel member connected to the base and having a proximal end and a distal end, wherein the proximal end reversibly attaches to the base in one of two positions; and
    a stem connected to the keel member and having a stem attachment extending from a first end, wherein the stem attachment reversibly attaches to the distal end of the keel member in one or two positions and wherein the stem attachment extends at an angle from the first end.

2. The component as defined in claim 1 wherein the base includes a boss extending therefrom and a non-circular shaped recess adjacent the boss, and wherein the proximal end of the keel member includes a recess for receiving the boss and also includes fins adjacent the recess for engaging the shaped recess adjacent the boss.

3. The component as defined in claim 1 wherein the distal end of the keel member includes a recess that slidingly receives the stem attachment.

4. The component as defined in claim 3 wherein the distal end of the keel member includes at least one tab, and wherein the first end of the stem includes at least one notch for engaging the tab and providing anti-rotation between the keel member and the stem.

5. The component as defined in claim 1 wherein the stem attachment extends at an angle of about 7 degrees from the first end.

6. A reversible tibial component comprising:
    a base having a centroidal axis extending therethrough;
    a keel member attached to the base in one of a first and a second position, wherein the first and second positions are reversible; and
    a stem removably connected to the keel member and having a proximal end that slidingly and anti-rotationally engages the keel member in one of two reversible positions, and wherein the keel member offsets the stem from the centroidal axis of the base.

7. The component as defined in claim 6 wherein the stem has an elongated body and has a stem attachment that engages the keel member and that extends outwardly at an angle from the body at the proximal end.

8. The component as defined in claim 7 wherein the stem attachment has a threaded internal bore, the keel member and the base include an aperture extending therethrough, and the tibial component further comprises a threaded fastener that extends into the aperture and threadably engages the threaded internal bore of the stem.

9. A tibial prosthetic implant with a reversible offset stem comprising:
- a base;
- a first connector on the base;
- a reversible keel member having a first end attached to the first connector and a second end including an offset stem receiver; and
- a stem having an angled attachment formed therewith and connected to the offset stem receiver, wherein the keel member includes first orientation locators and the stem includes second orientation locators for engagement with the first orientation locators, wherein the orientation locators limit orientation of the stem on the keel member, and wherein the stem includes a slot formed in the distal end thereof.

10. The implant as defined in claim 9 wherein the slot is limited to extend in an anterior-posterior direction.

11. The implant as defined in claim 10 wherein the stem is tapered at the distal end adjacent the slot.

12. The implant as defined in claim 11 wherein the stem is secured to the base by a fastener.

13. The implant as defined in claim 12 wherein the fastener extends through the first connector and the offset stem receiver.

* * * * *